United States Patent [19]
Waletzko

[11] Patent Number: 4,617,706
[45] Date of Patent: Oct. 21, 1986

[54] DEVICE FOR MANIPULATING CADAVERS
[76] Inventor: Wallace Waletzko, Box 180, Avon, Minn. 56310
[21] Appl. No.: 759,863
[22] Filed: Jul. 29, 1985
[51] Int. Cl.⁴ .................. A61G 1/00; A61G 7/10; A61G 19/00
[52] U.S. Cl. ............................. 27/28; 27/12; 5/82 R
[58] Field of Search ............... 27/27, 28, 12; 5/82 R, 5/81 R

[56] References Cited
U.S. PATENT DOCUMENTS

| | | | |
|---|---|---|---|
| 524,824 | 8/1894 | Hiser | 27/28 X |
| 616,282 | 12/1898 | Allen | 27/28 X |
| 821,720 | 5/1906 | Kidd | 27/28 |
| 1,205,186 | 11/1916 | Fuchs | 5/82 R |
| 1,224,383 | 5/1917 | Jones | 27/27 X |
| 1,240,359 | 9/1917 | O'Reilly | 5/82 R |
| 2,187,198 | 1/1940 | Fields | 27/28 X |
| 2,203,732 | 6/1940 | Kubach | 27/28 |
| 2,449,898 | 9/1948 | Hower | 27/28 X |
| 2,564,333 | 8/1951 | Kelly | 296/20 |
| 2,638,657 | 5/1953 | Arnold | 27/28 |
| 3,273,219 | 9/1966 | Tuschen | 27/28 X |
| 3,396,414 | 8/1968 | Niveau | 5/81 R |
| 3,426,367 | 2/1969 | Bradford | 5/82 R |
| 3,574,871 | 4/1971 | Greene | 5/82 R |
| 3,757,359 | 9/1973 | Stellman | 5/81 R |

Primary Examiner—Robert A. Hafer
Assistant Examiner—Terrence L. B. Brown
Attorney, Agent, or Firm—Orrin M. Haugen; Thomas J. Nikolai

[57] ABSTRACT

A device for manipulating cadavers is described incorporating a support apparatus and a harness apparatus. The support apparatus is comprised of two side rails assemblies, a foot rail assembly and a head rail assembly. The harness apparatus, which is secured to the support apparatus by a plurality of hooks is comprised of at least two upside down, generally U-shaped brackets which are joined at their apex by an axle. Slidably associated with the axle are means by which the apparatus can be lifted by an overhead crane. The design permits the apparatus to be easily and quickly assembled and disassembled by the mortician. It also permits the mortician to work on the cadaver without interference from the apparatus itself.

3 Claims, 3 Drawing Figures

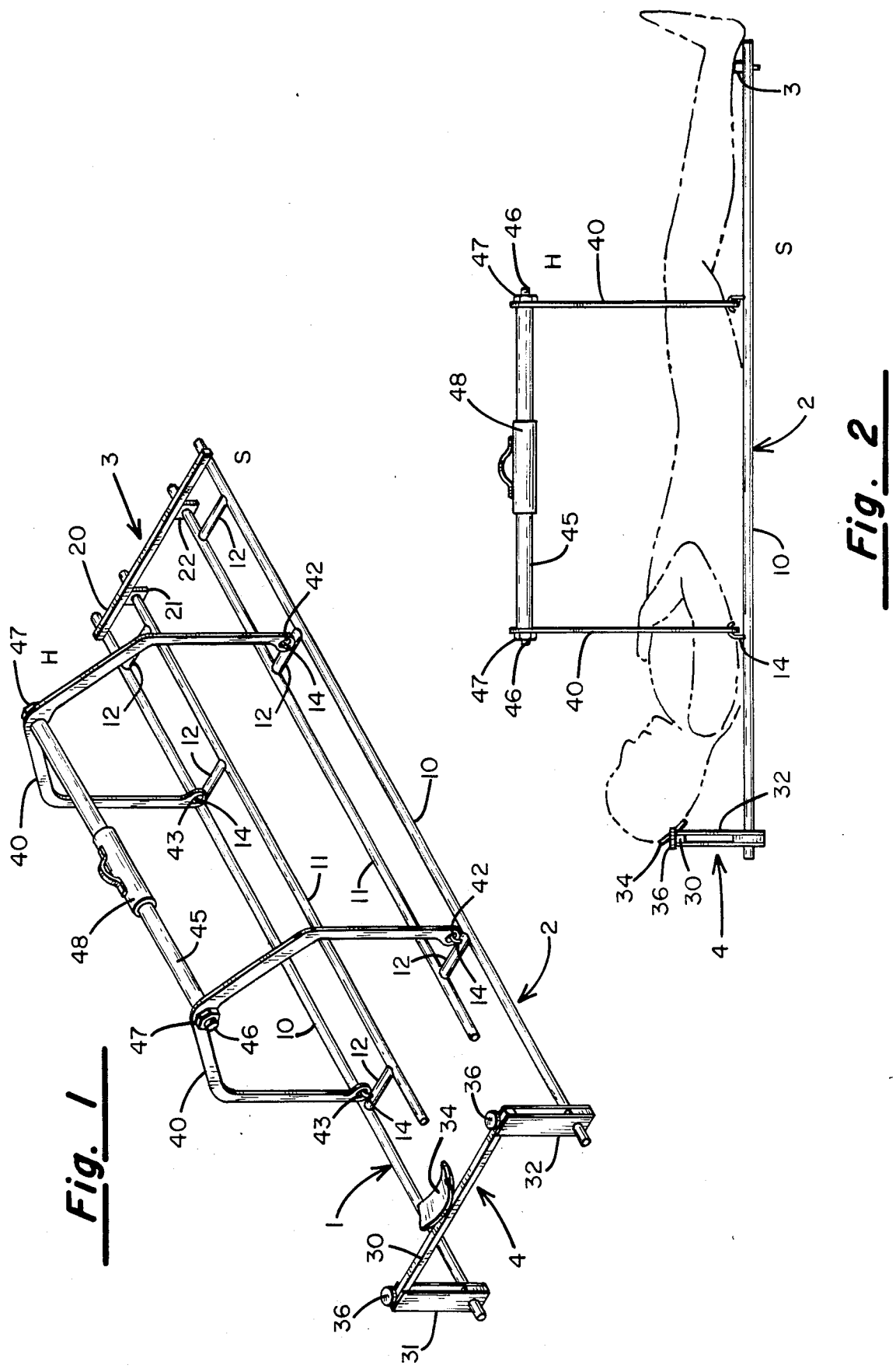

DEVICE FOR MANIPULATING CADAVERS

BACKGROUND OF THE INVENTION

I. Field of the Invention

This invention relates generally to a device for manipulating cadavers, and more particularly to a device intended for use by a mortician for transporting and manipulating cadavers within a mortuary work room.

II. Discussion of the Prior Art

For many years, morticians have been faced with problems associated with lifting, moving and manipulating cadavers as they are being prepared for internment. In that this process generally includes embalming, grooming and dressing and cadaver as well as placing the cadaver in a casket, the cadaver must be moved several times during the preparation process and must be fully supported during each move.

Several devices have been developed for use in preparing corpses for burial. One such device is disclosed in U.S. Pat. No. 821,720 which issued on May 29, 1906 to G. E. Kidd. The Kidd Patent discloses a device which is similar to those commonly used in the mortuary industry today. This device includes two side bars 1 and two end bars 3 as well as a plurality of straps 10 which support the corpse as it is being lifted and moved. U.S. Pat. No. 2,449,898 to Hower shows a similar type structure in which straps extending beneath the body are again used to support while it is being lifted and moved.

Another type of device used for the movement of corpses is shown in U.S. Pat. No. 1,240,359 to O'Reilly which was granted on Sept. 18. 1917. This patent discloses a device which has an upper frame as well as a bag 41 extending beneath the frame which contains the corpse. The bag is divided into two sections with each section having eyelets 50. A cord 51 is weaved through the eyelets as shown best in FIG. 2 to hold the two sides of the bag together. When it is desired to remove the corpse from the bag, the cord 51 is released and pulled through all the eyelets.

Still another device which has been used in the mortuary industry for lifting and moving corpses is shown in U.S, Pat. No. 2,203,732 to Kubach which issued on June 11, 1940. This device can generally be described as having a certain bar which runs parallel to the length of the body. Extending perpendicular to the bar and spaced from each other are a plurality of bow-shaped rods having terminal hooks on each of their respective ends. Associated with each such bow-shaped rod is a strap which is threaded under the body and helps support it. Eyelets on each end of the strap are slipped over the hooks when in use. The Kubach Patent also discloses means for securing the device to a block and tackle which can be used to lift the corpse using an overhead crane.

While each of the above-described devices have been used in the mortuary industry for some time, they all suffer from one serious drawback, namely the use of straps or a bag makes assembly and disassembly of the device extremely inconvenient. With each of the prior art devices described above, the corpse must be repeatedly rolled and turned during assembly and disassembly. When this is done during disassembly, it requires additional grooming of the corpse and the like.

SUMMARY OF THE INVENTION

The present invention is deemed to be an improvement over the prior art devices described above. Rather than having a sheet or plurality of straps which are slid beneath the entire width of the body, the device of the present invention has left and right slide rail assemblies which are slid beneath the body along each side thereof. Also present are foot rail and head rail assemblies which are slipped onto the side rail assemblies and are locked into place in the proper position along the side rail assemblies by set screws.

The device of the present invention also includes a harness comprised of two upside down generally U-shaped brackets which extend upwardly from and are hooked to the side rail assemblies. Extending between the two U-shaped brackets at their apex is an axle which has a member slidably secured to it so that an appropriate balancing point can be reached. This member has means by which it can be hooked to an overhead crane for use in moving the entire assembly and cadaver.

The present invention has many advantages. These include:

(1) The ability to assemble the device without having to repeatedly rotate or turn the cadaver;

(2) The ability to prepare the cadaver for burial without the device getting in the way;

(3) The ability to lift and move the cadaver using the overhead crane; and (4) The ability to disassemble the device in the confined space of a coffin without mussing the cadaver to the extent that a great deal of additional grooming will be required.

OBJECTS

It is accordingly a principal object of the present invention to provide a new and improved device whereby cadavers can be manipulated and moved during preparation for burial.

Another object of the invention is to provide a device which can easily and quickly be assembled around a cadaver in such a way that it does not require a great deal of turning or moving of the cadaver.

Yet another object of the invention is to provide a device which will permit lifting and moving of the cadaver with an overhead crane.

Still another object of the invention is to provide such a device which can be quickly and easily disassembled within the confines of a casket without disturbing the cadaver to the point where additional grooming will be required.

These and other objects and advantages will become apparent to those skilled in the art from the following detailed description of the preferred embodiment, especially when considered in conjunction with the accompanying drawing in which like numerals in the several views refer to corresponding parts.

DESCRIPTION OF THE DRAWINGS

FIG. 1 is a perspective view of an assembled device embodying the invention;

FIG. 2 is a plan view showing the separate frame members of the apparatus of the present invention connected and positioned around a cadaver which is shown in a reclining position;

DESCRIPTION OF THE PREFERRED EMBODIMENT

Figure 3:
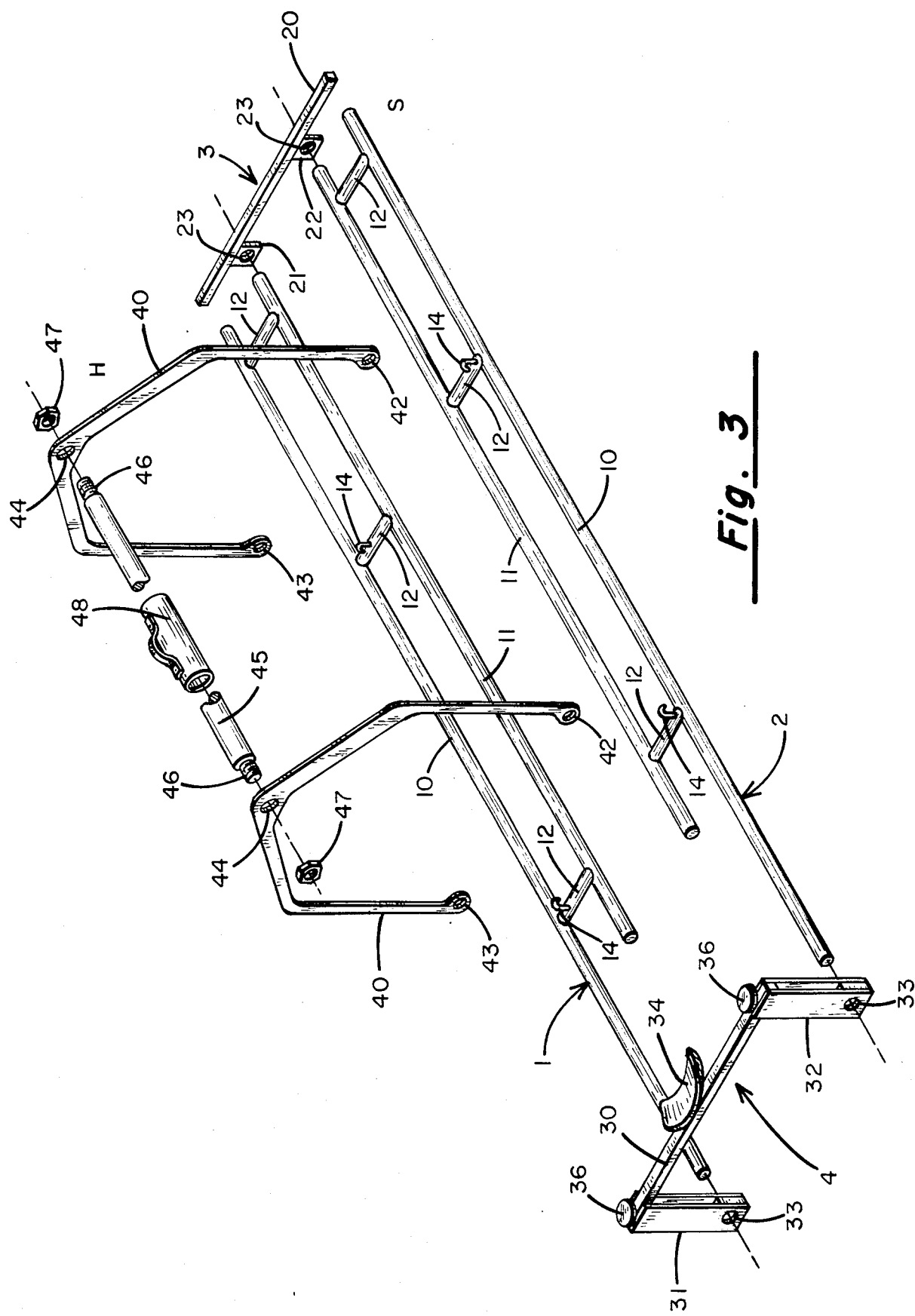
FIG. 3 is a exploded perspective view of the apparatus of the present invention.

Briefly, the apparatus of the present invention comprises a support apparatus S and a harness apparatus H which are shown in the drawings. As shown in FIG. 3, the support apparatus S is comprised of two complementary, longitudinal side rail assemblies 1 and 2, a foot rail assembly 3 and a head rail assembly 4. Each side rail assembly is comprised of two longitudinally extending bars 10 and 11 which are joined together by a plurality of support bars 12. These support bars 12 are generally perpendicular to the longitudinally extending bars 10 and parallel to each other. Projecting upwardly from at least two of said support bars on each side rail assembly 1 or 2 is a hook member 14 which is used to engage the harness member H. In the preferred embodiment, the inner longitudinal bars 11 are made shorter than bars 10 so that they do not interfere with the pillow in a conventional casket.

The foot rail assembly 3 is comprised of a bar 20 which has at least two projections 21 and 22 extending therefrom. Each projection has an annular bore 23, which is capable of slidably receiving and retaining a longitudinal support bar 11 of the side rail assemblies 1 and 2. As shown clearly in FIG. 1, bar 20 is long enough so that its bottom engages each of the two longitudinal support bars 10 when the apparatus is assembled. The foot rail assembly is held in place with respect to the side rail assemblies by the weight of the cadaver's legs. The foot rail assembly is thus able to prevent the inner bar 11 of the side rail assemblies 1 and 2 from pivoting downwardly and outwardly with respect to the bar 10 of side rail assemblies 1 and 2 as the apparatus and cadaver are lifted.

The head rail assembly 4 has a bar 30 and two projections 31 and 32 extending in the same direction therefrom. Each of these projections has an annular bore 33 which is capable of receiving a longitudinal bar 10 of the side rail assemblies 1 and 2. Set screws can be used to lock the head rail assembly 4 in place with respect to the side rail assemblies 1 and 2.

Also secured to the bar 30 of the head rail assembly 4 is a cup 34 which is used to support the head of the cadaver. Screws with hand knobs 36 are present to lock the head rail assembly 4 to the two side rail assemblies 1 and 2.

Harness H includes two U-shaped brackets 40. Each U-shaped bracket 40 has three annular bores 42–44 through it. Bores 42 and 43 are near the ends of the legs of the U-shaped bracket 40 and are present for receiving the hooks 14 which are secured to the side rail assemblies 1 and 2. The third bore 44 on each U-shaped bracket 40 is present for receiving the threaded ends 46 of lateral axle 45. Axle 45 is secured to the two U-shaped brackets 40 by means of nuts 47. Axle 45 is also long enough to apply sufficient tension to the U-shaped brackets 40 so that they do not become disassociated from hooks 14 as the apparatus of the present invention is being used. Present in slidable and rotatable engagement with said axle 45 is a member 48 by which the present invention can be hooked to a conventional overhead crane which is used for moving the entire assembly and the cadaver.

When the present invention is in use, the cadaver is laid upon a table. One side of the cadaver is then lifted slightly so that the side rail assembly 1 can be placed under the appropriate side of the cadaver. The cadaver is then turned slightly in the opposite direction so that the other side rail assembly 2 can be put in place under the other side of the cadaver. The foot rail assembly 3 is then slipped over the lateral support bars 11 of the side rail assembly. Likewise, the head rail assembly is slipped over the longitudinal support bars 10 and locked into place by the set screws.

Once the cadaver is properly positioned on the support apparatus S, the harness H is assembled. First, the U-shaped brackets 40 are secured to the side rail assemblies via the hook means 14 and the annular bores 42 and 43. The lift member 48 is slid over the axle 45. Each threaded end of axle 45 is then slipped into an opening 44 of one of the two U-shaped brackets 40 and locked in place using bolts 47.

As best shown in FIG. 2, when the cadaver is in place, the apparatus of the present invention does not interfere with the mortician's ability to work on the cadaver. Further, it becomes an easy matter for the mortician to use an overhead crane to lift the cadaver from work station to work station as it is being prepared for burial. The apparatus of the present invention can also be used to place the cadaver in a casket. Once the cadaver is in place, harness H can easily be removed from the support apparatus S with disassembling harness H by simply applying inward pressure to the U-shaped brackets 40 near their bottom until they become disassociated from hooks 14. The support apparatus is then disassembled by (a) loosening the set screws on the head rail assembly 4 using hand knobs 35, and (b) removing the foot rail assembly 3 and head rail assembly 4 from the side rail assemblies 1 and 2. Finally, the side rail assemblies 1 and 2 are removed from beneath the cadaver.

The invention has been described herein in considerable detail in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be accomplished without departing from the scope of the invention itself.

What is claimed is:

1. An apparatus for manipulating cadavers including support means for supporting the cadaver during movement and manipulation and harness means which cooperate with said support means wherein said support means include:
   (a) a first side rail assembly for supporting from beneath one side of said cadaver said side rail assembly being comprised of an outside longitudinal bar and a shorter inside longitudinal bar joined together by a plurality of support bars;
   (b) a second side rail assembly for supporting from beneath the other side of said cadaver, said second side rail assembly also being comprised of an outside longitudinal bar and a shorter inside longitudinal bar joined together by a plurality of support bars;
   (c) a foot rail assembly for supporting the feet of the cadaver comprised of a bar, said bar being long enough for its bottom to engage the outside longitudinal bars of the first and second side rail assemblies, and having a first projection extending therefrom associated with the inside longitudinal bar of the first side rail assembly and a second projection extending therefrom associated with the inside longitudinal bar of the second side rail assembly, each such projection having an annular bore slidably receiving and retaining in assembled relation one end of the inside longitudinal bar of the side rail assembly associated therewith;

(d) a head rail assembly comprised of a bar having cup means associated therewith for supporting the cadaver's head, a first projection extending therefrom associated with the first side rail assembly and the second projection extending therefrom associated with the second side rail assembly, each such projection having an annular bore for slidably receiving and retaining in assembled relation the other end of the outside longitudinal bar of the side rail assembly associated therewith; and (e) means for locking said head rail assembly in place with respect to said side rail assemblies.

2. The apparatus of claim 1 wherein said harness means include:
(a) a plurality of generally U-shaped brackets;
(b) means for securing said U-shaped brackets to said side rail assemblies;
(c) an axle extending between said generally U-shaped brackets; and
(d) means slidably and rotatably fixed to said axle for securing said harness to lifting means such as a crane.

3. The apparatus of claim 2 wherein said means for securing said U-shaped brackets to said side rail assemblies include annular openings in the legs of said U-shaped brackets which mate with hooks which are fixedly attached to said side rail assemblies.

* * * * *